(12) United States Patent
Nicholson et al.

(10) Patent No.: US 6,891,383 B2
(45) Date of Patent: May 10, 2005

(54) SOOT DETECTOR FOR ENGINE OIL

(75) Inventors: Warren Baxter Nicholson, El Paso, TX (US); Louis L. Nagy, Warren, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 10/649,531

(22) Filed: Aug. 27, 2003

(65) Prior Publication Data

US 2005/0057267 A1 Mar. 17, 2005

(51) Int. Cl.⁷ .............................................. G01R 27/08
(52) U.S. Cl. ...................................... 324/698; 324/643
(58) Field of Search ................................. 324/643, 698

(56) References Cited

U.S. PATENT DOCUMENTS

| | | | |
|---|---|---|---|
| 4,345,202 A | 8/1982 | Nagy et al. | ............ 324/58.5 B |
| 4,503,384 A | 3/1985 | Nagy et al. | ................ 324/61 P |
| 4,543,823 A | 10/1985 | Nagy et al. | ............... 73/304 C |
| 4,544,880 A | 10/1985 | Nagy et al. | ............ 324/58.5 R |
| 4,862,060 A * | 8/1989 | Scott et al. | .................. 324/639 |
| 4,902,961 A * | 2/1990 | De et al. | .................... 324/640 |
| 5,027,076 A * | 6/1991 | Horsley et al. | ............. 324/674 |
| 5,604,441 A * | 2/1997 | Freese et al. | ............... 324/663 |
| 5,656,767 A * | 8/1997 | Garvey et al. | ............. 73/61.44 |
| 5,754,055 A * | 5/1998 | McAdoo et al. | ............ 324/636 |
| 6,268,737 B1 * | 7/2001 | Marszalek | .................. 324/663 |
| 6,377,052 B1 * | 4/2002 | McGinnis et al. | .......... 324/446 |
| 6,459,995 B1 * | 10/2002 | Collister | ...................... 702/23 |
| 2003/0132740 A1 * | 7/2003 | Stone et al. | ............... 324/71.4 |
| 2004/0135585 A1 * | 7/2004 | Nagy | ......................... 324/643 |

* cited by examiner

*Primary Examiner*—Charles H. Nolan, Jr.
(74) *Attorney, Agent, or Firm*—Jimmy L. Funke

(57) ABSTRACT

A method and apparatus for detecting the concentration of soot particles in engine oil. A microwave signal having a varying frequency is applied to a transmission line having a probe tip exposed to the engine oil. A voltage is read at a stationary detection point along the length of the transmission line for each applied frequency. The applied frequency when the probe voltage is equal to a null voltage of a standing wave within the transmission line is compared to a reference frequency determined when the probe voltage is equal to a null voltage for a known concentration of soot particles. The concentration is calculated based upon the result of the comparison. Preferably, a reference probe receives the same input signal. A known relationship between the reference probe and the transmission line is then used to eliminate temperature effects on the applied frequency.

31 Claims, 3 Drawing Sheets

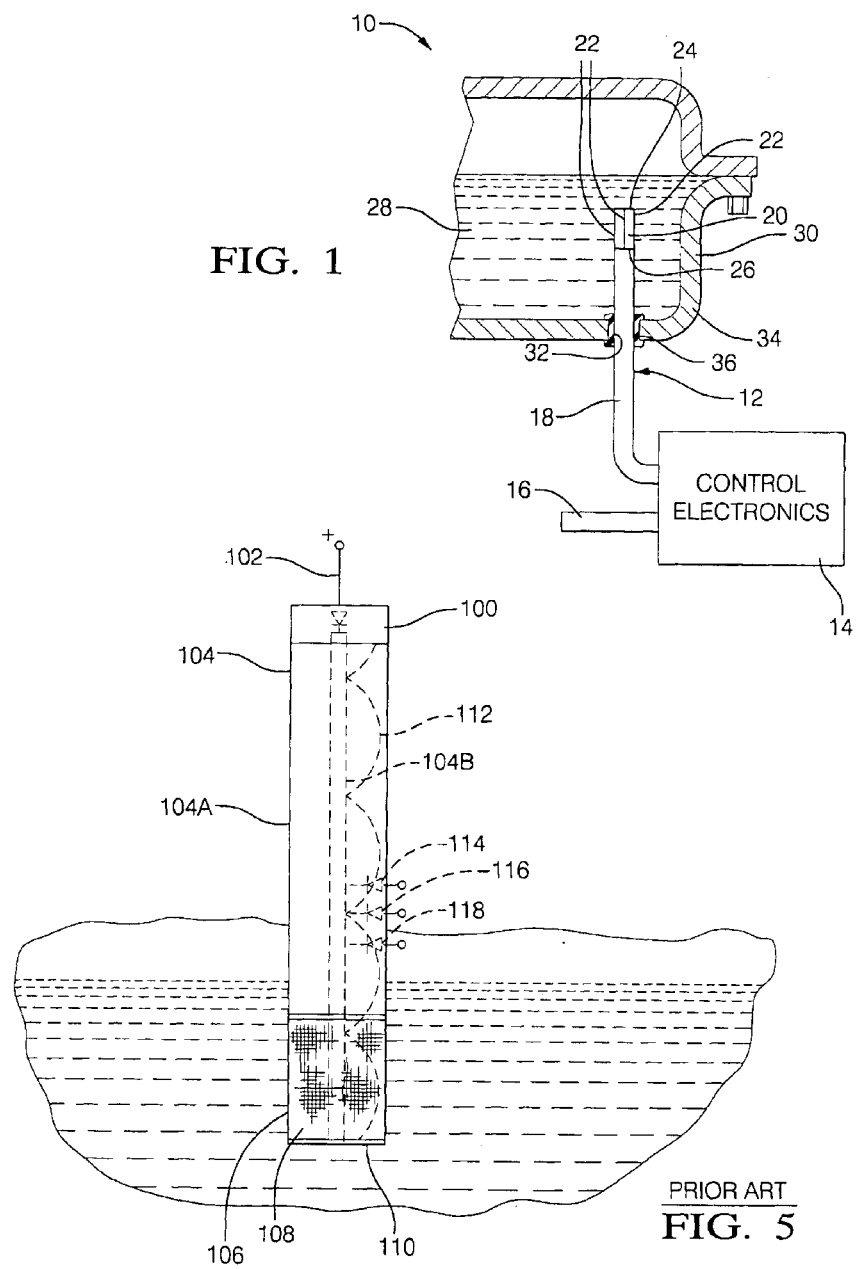

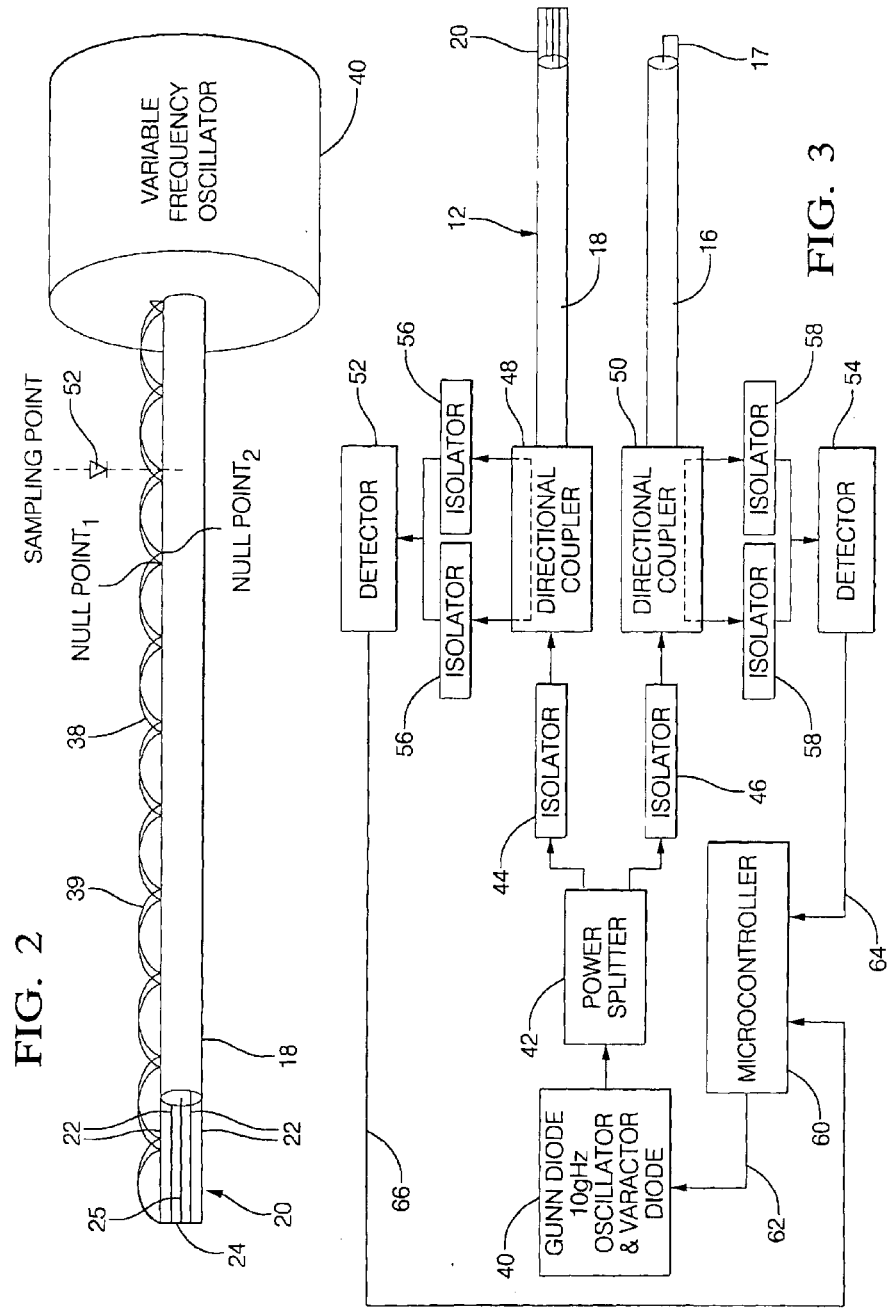

ately measuring the relative permittivity of engine oil is a prior art method of
SOOT DETECTOR FOR ENGINE OIL

TECHNICAL FIELD

The invention relates to sensors and, more particularly, to a method and apparatus for detecting soot in engine oil.

BACKGROUND OF THE INVENTION

Soot is a product of combustion in the combustion chamber of an engine, and it transfers in small amounts to crankcase oil in an engine, particularly a diesel engine. Thus, during operation of an engine, oil gradually builds up soot. When soot in the oil reaches an unacceptable level, the lubricating ability of the oil is diminished. Thus, measuring the soot content in oil over time is desirable as an indicator of the need to replace the oil.

Soot particles are very fine conductive particles. Despite this conductivity, they can increase the relative permittivity or relative dielectric constant of a dielectric fluid, such as oil, by acting as an artificial dielectric. Thus, one method of determining the soot content of oil involves measuring relative permittivity, such as taught in expired U.S. Pat. No. 4,345,202 to Nagy et al., the entire contents of which is incorporated herein by reference.

FIG. 5 shows an apparatus used in the method of Nagy et al. A Gunn oscillator 100 receives a supply voltage from a voltage supply line 102 coupled to one end of a sealed coaxial transmission line 104 having outer and inner conductors 104A and 104B, respectively. The other end of the transmission line 104 comprises a probe 106 having the same inner conductor 104B as line 104 and an outer conductor 108 made from a fine mesh screen connected to outer conductor 104A. The bottom of the probe 106 is shorted by a conductor such as a mesh screen 110, and the probe 106 is immersed in the engine oil. Microwave energy from the oscillator 100 is reflected back by the short 10 to produce a standing wave 112 within the transmission line 104. A diode detector is physically moved along a transmission line to find a voltage null in the standing wave, which null changes with the percentage of soot. In FIG. 5, a plurality of microwave diode detectors 114, 116 and 118 are longitudinally spaced along the transmission line 104 for illustrative purposes. When the location of the null voltage is found, it is compared to the location of the null voltage point with no soot in the oil. From this comparison, the level of soot in the oil is determined.

While the teachings of Nagy et al. were applied easily in laboratory settings, their implementation in an actual automotive sensor proved difficult.

SUMMARY OF THE INVENTION

The present invention detects the level of soot in engine oil. In a preferred embodiment, a diode detector is used, but requirement of Nagy et al. that the diode detector physically move to detect levels has been removed. The apparatus and method described herein also optionally compensates for temperature variations that can effect the null point.

Broadly, one embodiment of the present invention is a method for detecting a concentration of soot particles in engine oil. The method comprises the step of applying a microwave signal having a frequency within a range of frequencies to one end of a transmission line having a probe tip at a second end of the transmission line where the probe tip is exposed to the engine oil. The method also includes the steps of detecting a probe voltage at a stationary detection point along an axial length of the transmission line for selected frequencies within the range of frequencies and determining a probe frequency of the selected frequencies when the probe voltage is equal to a null voltage of a standing wave within the transmission line. Further, the method includes the step of comparing the probe frequency to a probe reference frequency, wherein the probe reference frequency is a frequency of the microwave signal when the probe voltage is equal to a null voltage for a known concentration of soot particles in the engine oil. Finally, the method includes the step of calculating the concentration of soot particles in the engine oil based upon a result of the comparing step.

A second embodiment of the present invention is an apparatus for apparatus for detecting a concentration of soot particles in engine oil. The apparatus comprises means for applying a microwave signal having a frequency within a range of frequencies to one end of a transmission line having a probe tip at a second end of the transmission line. The probe tip is exposed to the engine oil. The apparatus also includes means for detecting a probe voltage at a stationary detection point along an axial length of the transmission line for selected frequencies within the range of frequencies and means for determining a probe frequency of the selected frequencies when the probe voltage is equal to a null voltage of a standing wave within the transmission line. Finally, the apparatus includes means for comparing the probe frequency to a probe reference frequency, wherein the probe reference frequency is a frequency of the microwave signal when the probe voltage is equal to a null voltage for a known concentration of soot particles in the engine oil, and means for calculating the concentration of soot particles in the engine oil based upon a result of the comparing step.

Other applications of the present invention will become apparent to those skilled in the art when the following description of the best mode contemplated for practicing the invention is read in conjunction with the accompanying drawings.

BRIEF DESCRIPTION OF THE DRAWING

The description herein makes reference to the accompanying drawings wherein like reference numerals refer to like parts throughout the several views, and wherein:

FIG. 1 is a schematic diagram of a soot detector with a soot probe in contact with engine oil according to one embodiment of the present invention;

FIG. 2 is a schematic diagram of the soot probe according to FIG. 1 connected to an oscillator;

FIG. 3 is a block diagram of a soot detector according to one embodiment of the present invention;

FIG. 5 is an apparatus used in a prior art method of measuring the relative permittivity of engine oil.

DESCRIPTION OF THE PREFERRED EMBODIMENT

Figure 4:
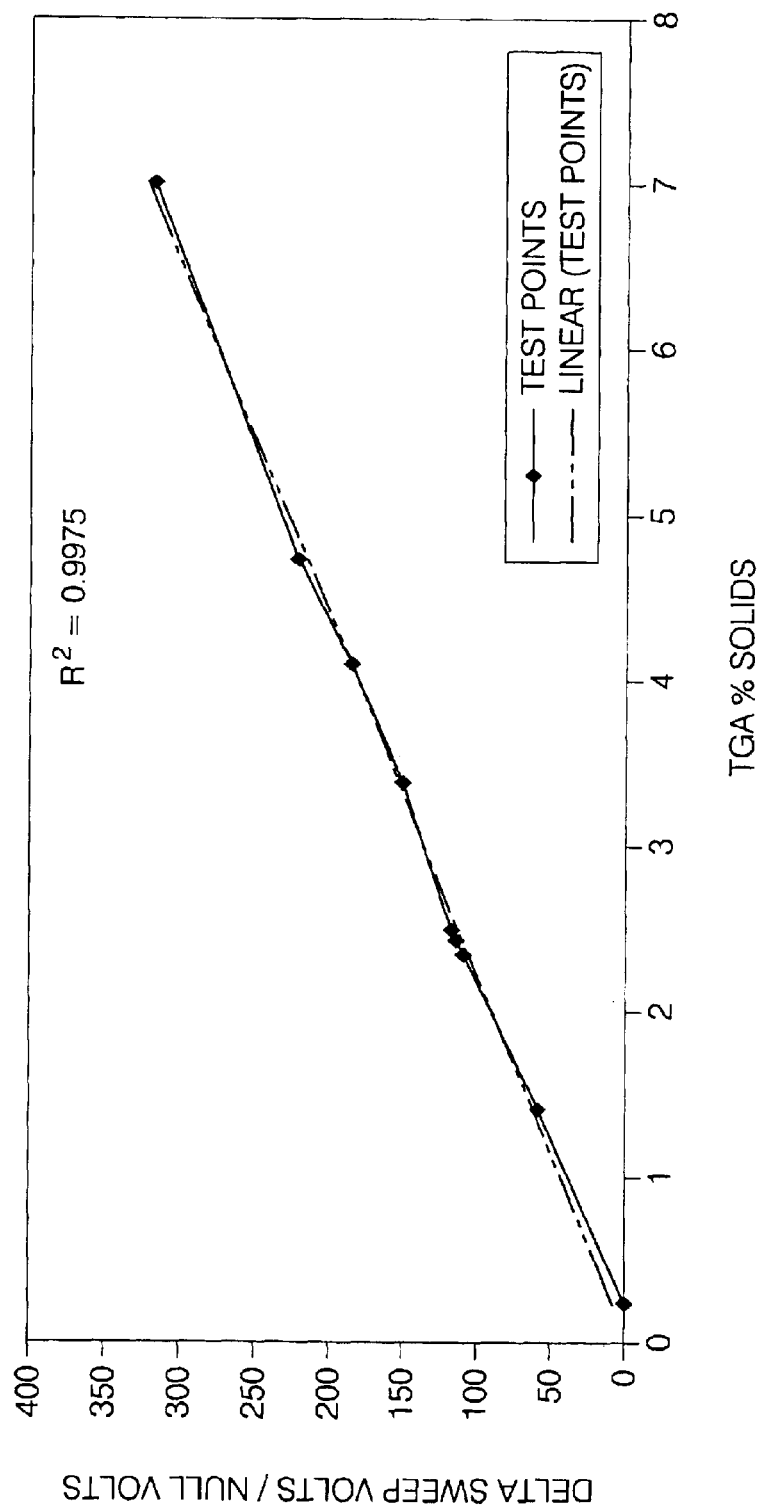
FIG. 4 is a graph showing the change in soot content versus the change in input voltage to the oscillator resonate circuit of FIG. 3 divided by the null voltage.

A soot detector illustrating the apparatus and method according to the present invention is described with reference to FIGS. 1–4. One embodiment of the soot detector 10 is shown in relationship with an oil pan 30 in FIG. 1. The detector 10 includes a soot probe 12 extending from control electronics 14 typically located in the passenger cabin (not shown). Thus, the soot probe 12 can be as long as a meter or more. In the preferred embodiment, a reference probe 16 also extends from the control electronics 14. The control electronics 14 and the reference probe 16 are described in more detail hereinafter. The soot probe 12 comprises a transmission line 18 and a probe tip 20. The transmission line 18 can be any transmission line that generally includes a pair of parallel conductors between which the signal voltage is applied, such as metal waveguides, coaxial lines, striplines, including microstrips, etc. and certain dielectric waveguides. Preferably, however, the transmission line 18 is a coaxial cable with, for example, a Teflon® dielectric.

The probe tip 20 can be one of any number of configurations. As illustrated, the probe tip 20 is formed by cutting the end of the transmission line 18, leaving a short extension of the center conductor 25 (shown in FIG. 2). The length of this extension is about a couple of centimeters. Of course, the center conductor of the probe tip 20 can be a separate conductor soldered to the center conductor 25 of the transmission line 18. Four wires 22 are soldered to the shield of the transmission line 18, preferably one wire every 90 degrees. In the embodiment shown, the wires 22 and the extension of the center conductor 25 are the same length and are soldered to a conductive disk 24. Alternatively, the four wires 22 are bent toward the center conductor 25, and all connections are soldered. It is possible for the dielectric of the transmission line 18 to allow the passage of oil. Thus, it is preferably that a small amount of the dielectric be removed and replaced by an epoxy material 26. The epoxy material 26 in the transmission line 18 prevents the passage of oil into the transmission line 18.

This probe tip 20 is a non-resonate transmission line extension and is similar to probe described in Nagy, et al., U.S. Pat. Nos. 4,345,202, 4,503,384, 4,543,823 and 4,544,880, each of which is incorporated herein in its entirety by reference. The open nature of this probe tip 20 allows the free flow of the engine oil being measured, while containing the generated energy field. An alternative to forming the probe tip 20 in this manner is to use a stripline as the probe tip 20.

The transmission line 18 is preferably a semi-rigid coaxial cable of a length sufficient so the probe tip 20 extends into the oil to be measured. Here, oil 28 fills an oil pan 30 secured to the engine crankcase 34 by known means. The transmission line 18 extends through an opening 32 in the oil pan 30 and is secured by an insulating washer 36. Of course, other ways of securing the transmission line 18 are possible within the level of skill of one in the art. Also, the use of the soot detector 10 in the oil pan 30 is exemplary only. The soot detector 10 can be used anywhere in the path of the oil through a vehicle.

FIG. 2 is a simplified schematic diagram generally illustrating the principles of the operation of the soot detector. In FIG. 2, a variable frequency oscillator 40 is coupled to the soot probe 12 at the end opposite the soot probe tip 20. By example, the oscillator 40 is a Gunn diode oscillator generating signals having a frequency in the X-band, that is a microwave signal having a frequency of eight to twelve GHz. However, higher frequency oscillators, such as oscillators generating signals with a microwave frequency of 24 GHz, are desirable. Frequencies lower than those in the X-band require longer soot probes, which are possible but impractical in automotive applications. Thus, in the application described herein, it is preferable that the oscillator 40 generate a microwave energy having a frequency no lower than an X-band frequency.

The oscillator 40 generates the microwave energy in the transmission line 18 and the probe tip 20. The short between the center conductor 25 and the four or more wires 22, caused by the conductive disk 24 in the illustrated embodiment, reflects back the energy, forming a standing wave in the soot probe 12 and the transmission line 18. As is known, the wavelength of a signal depends upon the transmission medium through which it travels. For any given wave frequency, the wavelength of a signal in a vacuum is equal to 300,000,000 m/sec divided by the frequency. The wavelength decreases outside of a vacuum for the same applied frequency. If a transmission line comprises a coaxial cable having a Teflon® dielectric, for example, the wavelength of a standing wave within the transmission line is 0.7 times the wavelength of the signal in a vacuum at the same applied frequency.

The wavelength through oil is equal to the wavelength in a vacuum times a velocity factor that varies with the percentage of soot in the oil. Specifically, $$\text{Wavelength}_{oil} = \frac{300{,}000{,}000 \text{ m/sec}}{\text{Frequency}} * \text{Velocity factor.}$$

Since the wavelength through a transmission line changes only with frequency according to the known relationship previously described, the only variable when the applied frequency and the wavelength of the standing wave in the entirety of the soot probe 12 are known is the percentage of soot in the oil.

The present invention takes advantage of these relationships as shown in the example of FIG. 2. A diode detector 52 is located at a fixed detection, or sampling, point to detect the voltage at the sampling point. Assume that the diode detector 52 detects a null voltage for the first standing wave 38 at the sampling point for a particular percentage of soot. For example, the diode detector 52 can be located at a known position along the axial length of the transmission line 18 so that a null voltage is detected at the sampling point when the percentage of soot is zero. At this first frequency generated by the oscillator 40, the wavelength of the standing wave 38 within the probe tip 20 is $\lambda_1$. The wavelength of the standing wave 38 in the transmission line 18 can be different. Null point, shows one location of the null voltage for the standing wave 38 in the transmission line 18.

As the percentage of soot in the oil increases, the propagation velocity (and the velocity factor) within the probe tip 20 changes. Thus, wavelength within the probe tip 20 changes from $\lambda_1$ even as the frequency remains the same. Of course, the wavelength within the transmission line 18 does not change if the frequency remains the same. However, the null point, i.e., the location of the null voltage, does. As shown in FIG. 2, for example, an increase in the percentage of soot results in a standing wave 39 within the probe tip 20 with a wavelength of $\lambda_2$. As the wavelength changes, the null points of the resultant standing wave 39 move axially along the transmission line 18. Null point$_2$ is one location of the null voltage for the standing wave 39 in the transmission line 18. The only way to bring the null point back to the sampling point, i.e., to sense the null voltage with the diode detector 52, is to change the frequency generated by the oscillator 40. The change in the frequency necessary to bring the null point back to the sampling point indicates the percentage of soot in the oil. Specifically, and as described in more detail hereinafter, a linear relationship can be developed between the change in frequency and the percentage of soot in the oil.

The preferred embodiment of the soot detector 10 is shown in block diagram form in FIG. 3. The variable frequency oscillator 40 shown is a Gunn diode oscillator operating in the X-band frequency range, selected because of its ready availability and relative low cost. Because such oscillators are typically temperature-sensitive, however, the soot detector 10 includes both the soot probe 12 previously described and a reference probe 16 as mentioned briefly with respect to FIG. 1. The use of the reference probe 16 for temperature compensation is discussed in more detail hereinafter. A varactor diode is part of the resonate circuit for the oscillator 40. The frequency of the oscillator 40 varies by the periodic application of a varying voltage, called a sweep voltage, to the varactor diode. As the sweep voltage applied to the varactor diode changes, the capacitance across the varactor diode changes, which in turn changes the resonate circuit and the output of the oscillator 40 to new frequencies according to known mathematical relationships. Although a varactor diode is used as part of the resonate circuit to vary the frequency of the oscillator 40, any circuit can be used to vary the frequency of the oscillator 40.

The output of the oscillator 40 is bifurcated with a power splitter 42. Isolators 44 and 46 respectively isolate the electromagnetic signals of the oscillator 40 and the power splitter 42 from the soot probe 12 and the reference probe 16. More specifically, the isolator 44 is connected at one end to the power splitter 42 and is connected to a first directional coupler 48 coupled to the soot probe 12. The isolator 46 is connected at one end to the power splitter 42 and is connected to a second directional coupler 50 coupled to the reference probe 16.

A first diode detector 52 for detecting the voltage at the stationary sampling point along the axial length of the transmission line 18 is coupled to the first directional coupler 48 through first parallel isolators 56. Similarly, a second diode detector 54 is coupled to the second directional coupler 50 through second parallel isolators 58. The second diode detector 54 detects the voltage at a stationary sampling point along the axial length of the reference probe 16. The voltage respectively read by each of the detectors 52, 54 is supplied to a controller including a processor, such as a microcontroller 60, which stores the values and determines the percentage of soot using those values. Although the controller is shown as a microcontroller 60, the controller can be, for example, a microprocessor with external memory or any equivalent circuitry that can perform the functions described herein.

The microcontroller 60 preferably generates the sweep voltage in the form of a ramp voltage through a digital-to-analog (D/A) converter, which is connected to the varactor diode frequency control of the oscillator 40. By example, the ramp voltage is a voltage that periodically ramps down from high of ten to 20 volts to a low of one volt. Alternatively, the ramp voltage is a triangular-shaped waveform that ramps up and down from the high voltage to the low voltage and back. The oscillator 40 sweeps through its frequency range in response to the sweep voltage and supplies microwave energy to each of the soot probe 12 and the reference probe 16.

As previously mentioned, the frequency of certain oscillators, particularly Gunn diode oscillators such as the oscillator 40, can vary with temperature. While the use of a reference probe 16 is not necessary, its use is desirable when a temperature-sensitive oscillator is used. The reference probe 16 is made of the same conductor as the transmission line 18 of the soot probe 12, preferably a coaxial cable having a Teflon® dielectric, so that a wave will propagate at the same rate as the transmission line 18. The reference probe 16 is also shorted at the end opposite the oscillator 40. Like the soot probe 12, the reference probe 16 can be shorted by a conductive disk soldered to the center conductor and the shield. In contrast, FIG. 3 shows the center conductive wire 17 of the reference probe 16 extending past the cut end. The conductive wire 17 is soldered to the shield. Of course, the conductive wire 17 can be a separate wire soldered between the center conductor and the shield of the transmission line that comprises the reference probe 16. The conductive wire 17 is shown extending from the end of the reference probe 16 only so that it is easily seen. If a conductive wire 17 is used to short the end of the reference probe 16, the conductive wire 17 should lie flush with the dielectric of the reference probe 16 between the center conductor and the shield.

The soot probe 12 as previously described can be as long as a meter or more to extend into the oil. The reference probe 16 can also be long enough to extend into the oil as shown in FIG. 3. However, the reference probe 16 can also be merely an inch or two, as shown in FIG. 1. The length of the reference probe 16 is, determined during calibration of the soot detector 10, which preferably occurs under zero soot conditions. As the sweep voltage applied to the varactor ramps down, the length of the reference probe 16 is adjusted so that a null voltage is detected first on the reference probe 16, then on the soot probe 12. The difference between the sweep voltage when a null point along the axial length of the reference probe 16 is detected and the sweep voltage when a null point along the axial length of the soot probe 12 is detected is stored in the microcontroller 60 as a calibration factor.

In operation, the oscillator 40 sweeps through its frequency range in response to the sweep voltage as previously described. The oscillator 40 supplies microwave energy to the soot probe 12 and the reference probe 16. For each voltage in the sweep voltage range, the second detector 54 detects the voltage at the sampling point of the reference probe 16. The DC reference output signal 64 is sampled through an analog-to-digital (A/D) input of the microcontroller 60 or is supplied to a digital input of the microcontroller 60 after passing through an A/D converter (not shown). Similarly, for each voltage in the sweep voltage range, the first detector 52 detects the voltage at the sampling point of the soot probe 12. The DC soot probe output signal 66 is sampled through another A/D input of the microcontroller 60, or is supplied to another digital input of the microcontroller 60 after passing through an A/D converter.

As the oscillator 40 sweeps through its frequency range, the microcontroller 60 checks each output signal 64, 66 for a null voltage. The difference between the sweep voltage when the second detector 54 senses a null voltage and the sweep voltage when the first detector 52 senses a null voltage at any given percentage of soot does not change due to temperature. Since the ambient temperature in the region of the oscillator 40 affects its output frequency, and an oscillator signal having the same frequency goes to both the soot probe 12 and the reference probe 16, the only variable is the velocity factor change due to the percentage of soot in contact with the probe tip 20. Thus, the change in the sweep voltage necessary for the first detector 52 to see a null point along the axial length of the soot probe 12 can indicate the percentage of soot in the oil without errors caused by possible temperature variations in frequencies output by the oscillator 40 when adjusted using the calibration factor previously stored. That is, any difference between the voltage applied to the varactor when the null voltage of the reference probe 16 is detected and the voltage applied to the varactor when the null voltage of the soot probe 12 is detected that is beyond the calibration factor is due solely to soot content. The sweep voltage has a known relationship to frequency, as described previously with respect to FIG. 2, so that the change in the sweep voltage to get back to a null point indicates the change in the frequency necessary to bring the null voltage back to the sampling point.

FIG. 5 is a graph showing the results of the method according to the invention compared to the standard Thermogravimetric analysis (TGA) method. The data in FIG. 5 is from a diesel engine run 300 hours with samples collected and measured using the TGA method at certain test points. The other axis of the graph is the change in sweep voltage applied to the varactor needed to get back to a null point as the percentage of soot changes. This difference in voltage is divided by the detected null voltage in volts. The null voltage is not zero; it is a low voltage usually in the millivolt range that is affected by the soot content. By dividing the change in sweep voltage by the null voltage, a linear relationship is revealed through which the soot content can be determined. Of course, an additional calculation can be performed to show the change in frequency instead of the change in voltage, but this is not necessary as the change in voltage represents the change in frequency according to the known relationship of the varactor input voltage to the frequency output of the oscillator.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for detecting a concentration of soot particles in engine oil comprising the steps of:
    applying a microwave signal having a frequency to one end of a transmission line having a probe tip at a second end of the transmission line and varying the frequency of the microwave signal within a range of frequencies, the probe tip being exposed to the engine oil;
    detecting a probe voltage at a stationary detection point along an axial length of the transmission line for selected frequencies within the range of frequencies;
    determining a probe frequency of the selected frequencies when the probe voltage is equal to a null voltage of a standing wave within the transmission line;
    comparing the probe frequency to a probe reference frequency, wherein the probe reference frequency is a frequency of the microwave signal when the probe voltage is equal to a null voltage for a known concentration of soot particles in the engine oil; and
    calculating the concentration of soot particles in the engine oil based upon a result of the comparing step.

2. The method according to claim 1 wherein the step of applying a microwave signal further comprises the step of applying a microwave signal having an X-band frequency to the one end of the transmission line.

3. The method according to claim 1 wherein the step of applying the microwave signal further comprises the step of:
    generating the frequency using a variable-frequency oscillator.

4. The method according to claim 3, further comprising the step of:
    applying a voltage within a range of voltages to a varactor diode of the variable-frequency oscillator wherein each voltage within the range of voltages results in a microwave signal having a unique one of the selected frequencies within the range of frequencies.

5. The method according to claim 4 wherein the probe frequency is represented by a first voltage applied to the varactor diode, and wherein the probe reference frequency is represented by a reference voltage, the reference voltage being a voltage applied to the varactor diode when the probe voltage is equal to the null voltage for the known concentration of soot particles in the engine oil.

6. The method according to claim 5 wherein the comparing step comprises the steps of calculating a difference of the first voltage and the reference voltage and dividing the difference by the null voltage of the standing wave within the transmission line.

7. The method according to claim 6 wherein the step of calculating the concentration of soot particles in the engine oil comprises the step of:
    comparing a result of the dividing step with a plurality of known values corresponding to known concentrations of soot particles.

8. The method according to claim 3, further comprising the step of:
    applying a ramp voltage signal to a varactor diode of the variable-frequency oscillator, wherein each voltage in the ramp voltage signal results in a microwave signal having a unique one of the selected frequencies within the range of frequencies.

9. The method according to claim 8 wherein the ramp voltage signal starts at a high value and ends at a low value, wherein the high value and the low value define the range of voltages.

10. The method according to claim 8 wherein the step of determining the probe frequency comprises the step of determining a first ramp voltage when the probe voltage is equal to the null voltage of the standing wave within the transmission line; and wherein the step of comparing the probe frequency to the probe reference frequency comprises the step of comparing the first ramp voltage to a probe reference voltage, the probe reference voltage being a voltage applied to the varactor diode that results in the probe reference frequency.

11. The method according to claim 10 wherein the step of comparing the first ramp voltage to the probe reference voltage comprises the steps of calculating a difference of the first ramp voltage and the probe reference voltage and dividing the difference by the null voltage of the standing wave within the transmission line.

12. The method according to claim 1 wherein the step of calculating the concentration of soot particles in the engine oil comprises the step of:
    comparing a result of the dividing step with a plurality of known values corresponding to known concentrations of soot particles.

13. The method according to claim 1, further comprising the step of:
    determining the probe reference frequency at a point when the known concentration of soot particles is zero.

14. The method according to claim 1 wherein the calculating step further comprises the step of comparing a result of the comparing step with a plurality of known values corresponding to known concentrations of soot particles.

15. The method according to claim 1 wherein the step of applying the microwave signal having the frequency within the range of frequencies further comprises the step of applying the microwave signal to one end of a reference probe having a short at a second end of the reference probe, the method further comprising the steps of:

detecting a reference probe voltage at a stationary detection point along an axial length of the reference probe for the selected frequencies within the range of frequencies;

determining a reference probe frequency of the selected frequencies when the reference probe voltage is equal to a null voltage of a standing wave within the reference probe;

comparing the reference probe frequency to a reference probe reference frequency, wherein the reference probe reference frequency is a frequency of the microwave signal when the probe voltage is equal to a null voltage for the known concentration of soot particles in the engine oil; and compensating for temperature variations in the first probe frequency using an output of the comparing step and a calibration factor.

16. The method according to claim 15 wherein the calibration factor is a difference between the probe reference frequency and the reference probe reference frequency.

17. The method according to claim 15, further comprising the steps of:

determining the probe reference frequency at a point when the known concentration of soot particles is zero;

determining the reference probe reference frequency at the point when the known concentration of soot particles is zero; and calculating the calibration factor by comparing the probe reference frequency to the reference probe reference frequency.

18. The method according to 15, further comprising the step of:

applying a voltage within a range of voltages to a varactor diode of a variable-frequency oscillator wherein each voltage within the range of voltages results in a microwave signal having a unique one of the selected frequencies within the range of frequencies.

19. The method according to claim 18 wherein a first probe voltage applied to the varactor diode represents the probe frequency; wherein a first reference probe voltage applied to the varactor diode represents the reference probe frequency; wherein a probe reference voltage represents the probe reference frequency, the probe reference voltage being a voltage applied to the varactor diode when the probe voltage is equal to a null voltage for the known concentration of soot particles in the engine oil; and wherein a reference probe reference voltage represents the reference probe reference frequency, the reference probe reference voltage being a voltage applied to the varactor diode when the reference probe voltage is equal to a null voltage for the known concentration of soot particles in the engine oil.

20. The method according to claim 18, further comprising the step of:

applying a ramp voltage signal to the varactor diode of the variable-frequency oscillator, the ramp voltage signal starting at a high value and ending at a low value, wherein each voltage in the ramp voltage signal results in a microwave signal having a unique one of the selected frequencies within the range of frequencies.

21. The method according to claim 20 wherein a null point of a standing wave within the reference probe is reached at a higher ramp voltage than a null point of a standing wave within the probe at any concentration of soot particles in the engine oil.

22. An apparatus for detecting a concentration of soot particles in engine oil comprising:

means for applying a microwave signal having a frequency to one end of a transmission line having a probe tip at a second end of the transmission line and for varying the frequency within a range of frequencies, the probe tip being exposed to the engine oil;

means for detecting a probe voltage at a stationary detection point along an axial length of the transmission line for selected frequencies within the range of frequencies;

means for determining a probe frequency of the selected frequencies when the probe voltage is equal to a null voltage of a standing wave within the transmission line;

means for comparing the probe frequency to a probe reference frequency, wherein the probe reference frequency is a frequency of the microwave signal when the probe voltage is equal to a null voltage for a known concentration of soot particles in the engine oil; and means for calculating the concentration of soot particles in the engine oil based upon a result of the comparing step.

23. The apparatus according to claim 22 wherein the means for applying a microwave signal comprises a variable-frequency oscillator.

24. The apparatus according to claim 23 wherein the variable-frequency oscillator is operable to apply microwave signals in a band higher than the X-band.

25. The apparatus according to claim 23, further comprising:

a reference probe having a short circuit at a first end, a second end of the reference probe operably connectable to the variable-frequency oscillator such that the microwave signal applied to the transmission line is simultaneously applied to the reference probe;

means for detecting a reference probe voltage at a second stationary detection point along an axial length of the reference probe for the selected frequencies within the range of frequencies;

means for determining a reference probe frequency of the selected frequencies when the reference probe voltage is equal to a null voltage of a standing wave within the reference probe;

means for comparing the reference probe frequency to a reference probe reference frequency, wherein the reference probe reference frequency is a frequency of the microwave signal when the probe voltage is equal to a null voltage for the known concentration of soot particles in the engine oil; and means for compensating for temperature variations in the first probe frequency using an output of the comparison and a calibration factor.

26. The apparatus according to claim 25 wherein the means for detecting the probe voltage further comprises a diode detector located at the stationary detection point along the axial length of the reference probe; and wherein the means for detecting the reference probe voltage further comprises a second diode detector located at the second stationary detection point along the axial length of the reference probe.

27. The apparatus according to claim 23 wherein the variable-frequency oscillator comprises a varactor diode operable to receive a voltage within a range of voltages, wherein each voltage within the range of voltages results in a microwave signal from the variable-frequency oscillator having a unique one of the selected frequencies within the range of frequencies.

28. The apparatus according to claim 27 wherein the probe frequency is represented by a first voltage applied to the varactor diode, and wherein the probe reference frequency is represented by a reference voltage, the reference voltage being a voltage applied to the varactor diode when the probe voltage is equal to the null voltage for the known concentration of soot particles in the engine oil.

29. The apparatus according to claim 28 wherein the means for comparing comprises means for calculating a difference of the first voltage and the reference voltage and means for dividing the difference by the null voltage of the standing wave within the transmission line.

30. The apparatus according to claim 29 wherein the means for calculating the concentration of soot particles in the engine oil comprises means for comparing a result of the dividing step with a plurality of known values corresponding to known concentrations of soot particles.

31. The apparatus according to claim 22 wherein the means for detecting a probe voltage further comprises a single, stationary diode detector.

* * * * *